(12) United States Patent
Robertson et al.

(10) Patent No.: US 9,622,726 B2
(45) Date of Patent: Apr. 18, 2017

(54) BIOPSY DEVICE LATCHING ASSEMBLY

(71) Applicant: HOLOGIC, INC., Marlborough, MA (US)

(72) Inventors: Daniel Robertson, Denver, CO (US); David VandeRiet, Lafayette, CO (US); Peter Wolton, Louisville, CO (US)

(73) Assignee: Hologic, Inc., Marlborough, MA (US)

( * ) Notice: Subject to any disclaimer, the term of this patent is extended or adjusted under 35 U.S.C. 154(b) by 353 days.

(21) Appl. No.: 14/555,468

(22) Filed: Nov. 26, 2014

(65) Prior Publication Data
US 2015/0150542 A1 Jun. 4, 2015

Related U.S. Application Data

(60) Provisional application No. 61/909,014, filed on Nov. 26, 2013.

(51) Int. Cl.
F16H 1/00 (2006.01)
A61B 10/02 (2006.01)

(52) U.S. Cl.
CPC .. *A61B 10/0233* (2013.01); *A61B 2010/0208* (2013.01); *Y10T 74/18704* (2015.01)

(58) Field of Classification Search
CPC ........ A61B 10/0233; A61B 2010/0208; F16H 1/16; F16H 35/063
See application file for complete search history.

(56) References Cited

U.S. PATENT DOCUMENTS

| | | | | |
|---|---|---|---|---|
| 2002/0045839 A1* | 4/2002 | Voegele | ............ | A61B 10/0275 600/564 |
| 2002/0082519 A1* | 6/2002 | Miller | ............ | A61B 10/025 600/566 |
| 2002/0156395 A1* | 10/2002 | Stephens | ............ | A61B 10/0275 600/567 |
| 2003/0018281 A1* | 1/2003 | Huitema | ............ | A61B 10/0275 600/567 |
| 2003/0216667 A1* | 11/2003 | Viola | ............ | A61B 10/0275 600/564 |
| 2007/0239067 A1* | 10/2007 | Hibner | ............ | A61B 10/0041 600/567 |
| 2012/0095366 A1* | 4/2012 | Heske | ............ | A61B 10/0233 600/566 |
| 2012/0265095 A1 | 10/2012 | Fiebig | | |

(Continued)

*Primary Examiner* — David M Fenstermacher
(74) *Attorney, Agent, or Firm* — Vista IP Law Group LLP

(57) ABSTRACT

A biopsy instrument driver includes a drive member having a laterally extending catch arm and movable between a distal, fired position and a proximal, armed position. A reversible motor has a rotatable output comprising or otherwise being operatively connected to a drive shaft, such that activation of the motor rotates the drive shaft. A translating member is threadably coupled to the drive shaft, wherein rotation of the drive shaft causes axial translation of the translating member along the drive shaft. A latch base is operatively associated with the translating member. A latch arm is pivotally coupled to the latch base, and has a distal portion configured to selectively engage and retain the drive member catch arm, and a proximal portion operatively coupled to the translating member, such that movement of the translating member relative to the latch base pivots latch arm distal portion.

11 Claims, 18 Drawing Sheets

(56) References Cited

U.S. PATENT DOCUMENTS

2015/0150542 A1\* 6/2015 Robertson .......... A61B 10/0233
  74/89.39
2016/0374650 A1\* 12/2016 Heske ................ A61B 10/0283
  600/566

\* cited by examiner

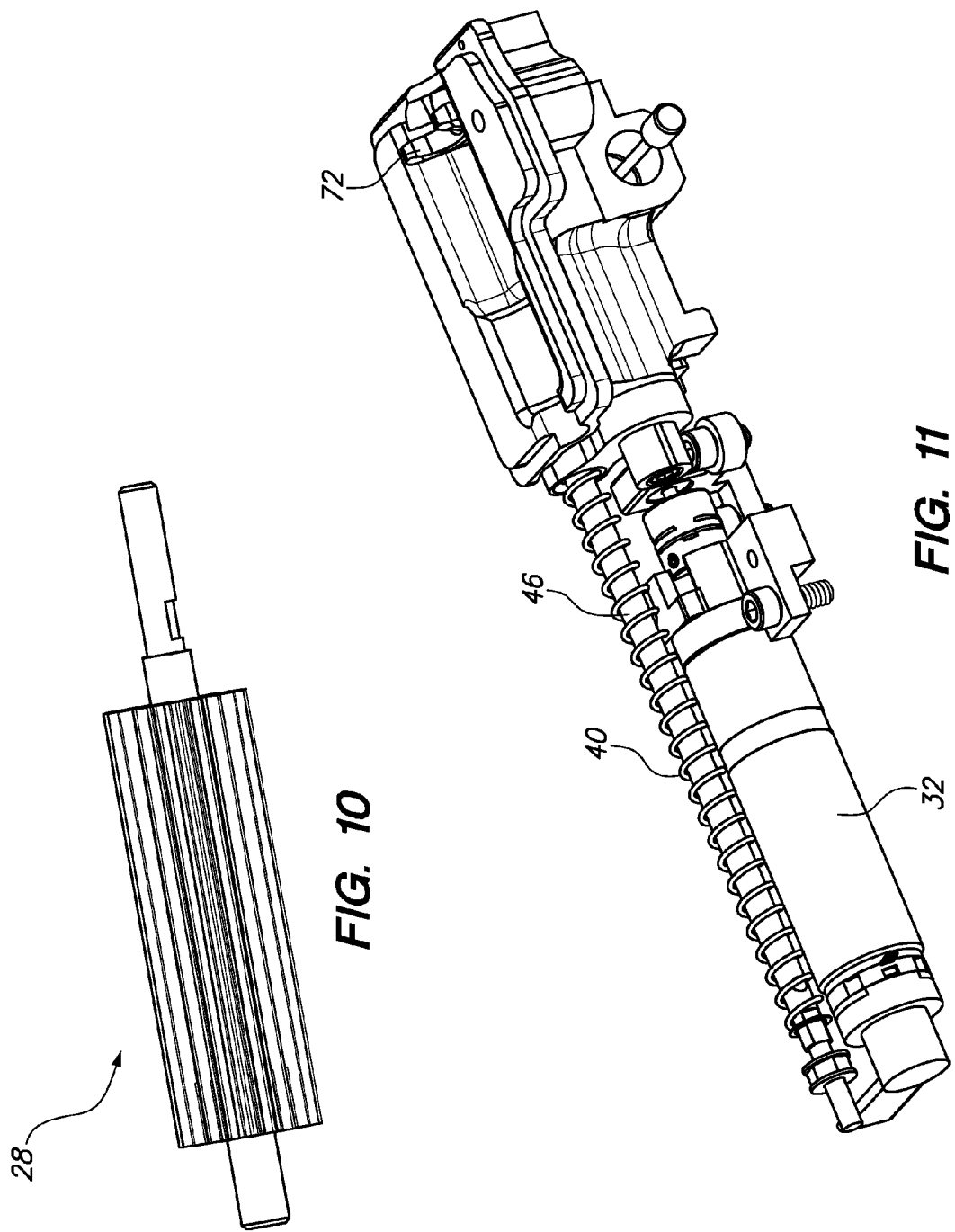

BIOPSY DEVICE LATCHING ASSEMBLY

RELATED APPLICATION DATA

The present application claims the benefit under 35 U.S.C. §119 to U.S. provisional patent application Ser. No. 61/909,014, filed Nov. 26, 2013. The foregoing application is hereby incorporated by reference into the present application in its entirety.

FIELD

The present disclosure generally relates to the field of tissue sampling and harvesting. More specifically, the disclosure relates to biopsy needle sets and devices.

BACKGROUND

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

Biopsies are routinely performed on tissue using a needle set, which typically includes an outer cannula defining a lumen and having a pointed tissue piercing tip and a proximal tissue receiving aperture. The needle set also includes an inner cannula slidably disposed within the outer cannula so that the aperture can be alternately opened and closed. The inner cannula has an open distal end with a cutting blade to excise tissue prolapsing through the aperture and into the lumen of the outer cannula. Typically, a hub is connected to the proximal end of each of the outer and inner cannulas. Such needle sets are used with or incorporated in various forms of biopsy devices, including motor driven biopsy devices.

Also, current motor driven biopsy devices can be larger than ideal due to the size of the components required to perform various steps of the biopsy. An overly large motor driven biopsy device can cause a biopsy procedure to be less than ideal. For instance, while ultrasound guided biopsy can be the most straightforward approach for guiding the biopsy device, lesions better seen on mammography images, particularly microcalcifications, require stereotactic localization. Stereotactic localization involves obtaining a pair of x-ray images. Thus, biopsy devices designed for stereotactic use must be sufficiently narrow to avoid interfering with the stereotactic localization pairs of x-ray images.

SUMMARY

In one embodiment, a biopsy instrument driver includes an instrument drive member coupled to a support structure and having a laterally extending catch arm, a motor coupled to the support structure and having a rotatable output, a drive shaft rotatably coupled to the support structure, a translating member threadably coupled to the drive shaft, a latch base movably coupled to the support structure and operatively associated with the translating member, and a latch arm movably coupled to the latch base. The drive member is movable relative to the support structure between a distal, fired position and a proximal, armed position. The drive shaft includes or is otherwise operatively connected to the motor output such that activation of the motor rotates the drive shaft. Rotation of the drive shaft causes axial translation of the translating member along the drive shaft relative to the support structure. The latch arm has a distal portion configured to selectively engage and retain the instrument drive member catch arm, and a proximal portion operatively coupled to the translating member, such that movement of the translating member along the drive shaft relative to the latch base moves latch arm distal portion.

In a single or multiple embodiments, the latch arm is coupled to the latch base by a pin, such that the latch arm may pivot about the pin relative to the latch base. The proximal portion of the latch arm may include a slot through which a peg extending from the translating member extends, such that movement of the translating member relative to the latch base causes a corresponding movement of the peg within the slot to thereby pivot the latch arm relative to the latch base between an open position and a closed position. The latch base may be movable relative to the support structure between a most-distal position and a most-proximal position. When the latch base is in the most-distal position and the drive member is in the fired position, the latch arm may be moved from the open position to the closed position to thereby retain the drive member catch arm. When the latch base is moved to the most-proximal position with the latch arm retaining the drive member catch arm, the drive member is thereby moved to its armed position.

In a single or multiple embodiments, the biopsy instrument driver also includes a firing spring operatively coupled to the drive member, where the firing spring is loaded as the drive member is moved from the fired position to the armed position. The biopsy instrument driver may also include a biasing spring interposed between the latch base and the translating member, the biasing spring applying a spring force to separate the latch base from the translating member.

In a single or multiple embodiments, the motor is a reversible output direction motor, such that activation of the motor in a first motor output direction moves the translating member along the drive shaft in a distal direction relative to the support structure, and activation of the motor in a second motor output direction opposite the first motor output direction moves the translating member along the drive shaft in a proximal direction relative to the support structure. The instrument driver may also include a controller configured to control activation and output direction of the motor.

In a single or multiple embodiments, the biopsy instrument driver also includes a solenoid configured to selectively prevent distal movement of the latch base when the latch base is in the most-proximal position, where the controller controls activation of the solenoid. The support structure may include or is otherwise coupled to a drive unit housing.

In a single or multiple embodiments, when the drive member is in the fired position, the controller is configured to arm the drive member by activating the motor in the first output direction to move the translating member in a distal direction relative to the support structure, thereby also moving the latch base in a distal direction via the biasing spring, until the latch base is in the most-distal position. Continued distal movement of the translating member compresses the biasing spring against latch base, with corresponding distal travel of the peg through the latch arm slot pivoting the latch arm into the open position. The controller is also configured to arm the drive member by activating the motor in the second output direction to move the translating member in a proximal direction relative to the support structure. The latch base remains in the most-distal position until the bias spring restores to a non-compressed state.

Activating the motor in the second output direction also causes corresponding proximal travel of the peg through the latch arm slot pivoting the latch arm into the closed position to thereby engage and retain the drive member catch arm. The peg thereafter pulls the respective latch arm, latch base, and drive member proximally in response to continued proximal movement of the translating member, until the latch base is in the most-proximal position and drive member in the armed position, with the firing spring in a loaded condition.

In a single or multiple embodiments, when the driver member is retained in the armed position by the respective latch arm and latch base, the controller is configured to fire the drive member distally by activating the solenoid to thereby retain the latch base in the most-proximal position to thereby prevent distal movement of the latch base relative to the support structure. The controller is also configured to fire the drive member distally by activating the motor in the first output direction to move the translating member in a distal direction relative to the latch member, thereby compressing the biasing spring and moving the peg distally through the latch arm slot to pivot the latch arm from the closed position to the open position, thereby releasing the drive member catch arm.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIG. 10 is a perspective view of a pinion of an inner cannula rotation mechanism according to one embodiment.

FIGS. 11, 13 and 14 are various perspective views of an outer cannula arming/firing mechanism according to one embodiment, with select components omitted for clarity.

DETAILED DESCRIPTION OF THE ILLUSTRATED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, he terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 1 to 4 depict various views of a bottom part 100 of a two-part biopsy device with the housing not shown. The bottom part 100 of the two-part biopsy device includes various carriages, gears, and motors for driving a needle set in the top part. The top part of the biopsy device may be configured to be "disposable," i.e., low cost to manufacture and detachable from the bottom part 100. The bottom part 100 may be configured to be "reusable," i.e., minimal to no contact with sterile surfaces and detachable from the top part.

Figure 1:
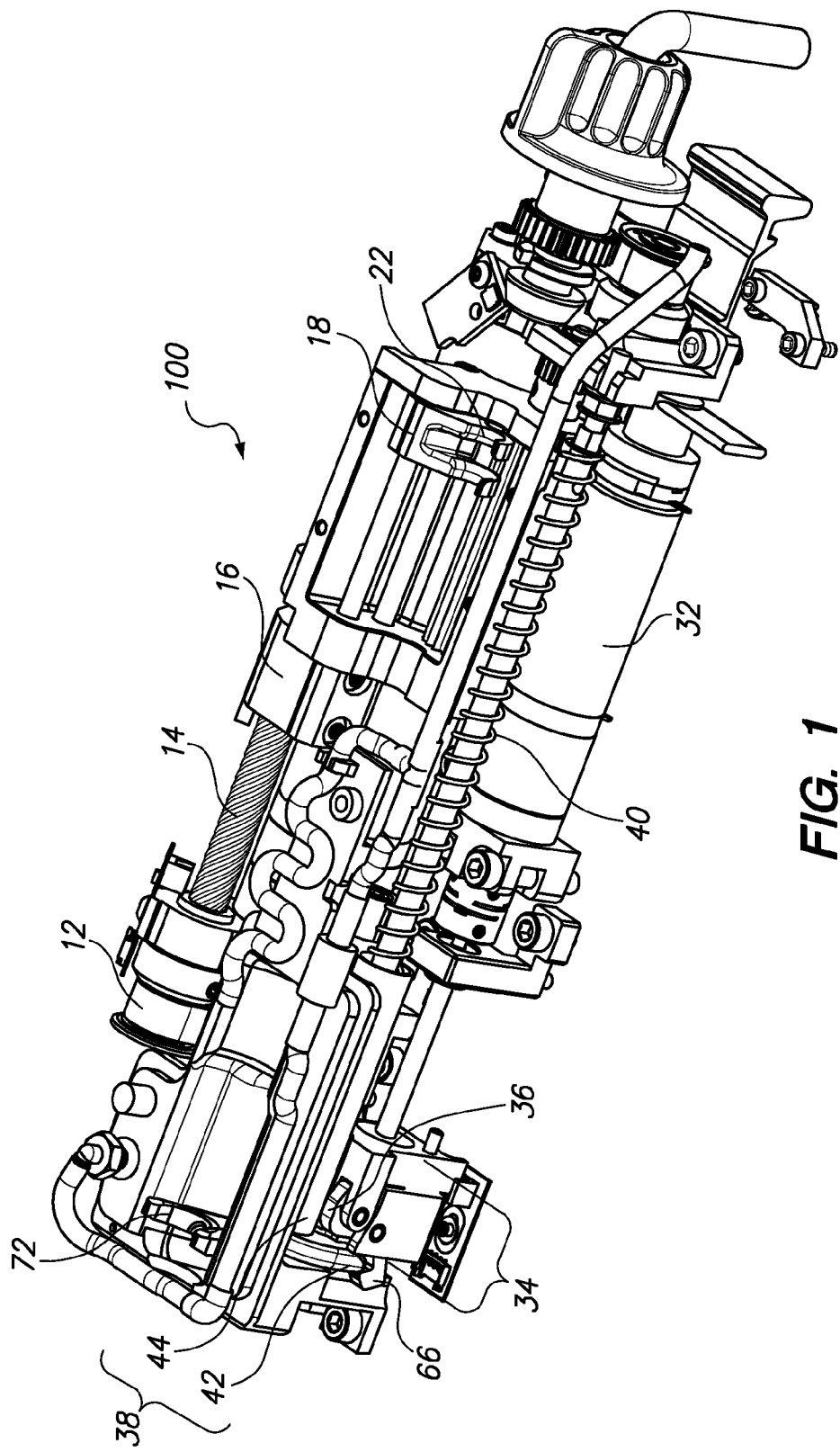
FIGS. 1 to 4 are various perspective views of the bottom portion of a two-part biopsy device according to one embodiment, with select components omitted for clarity.
Figure 2:
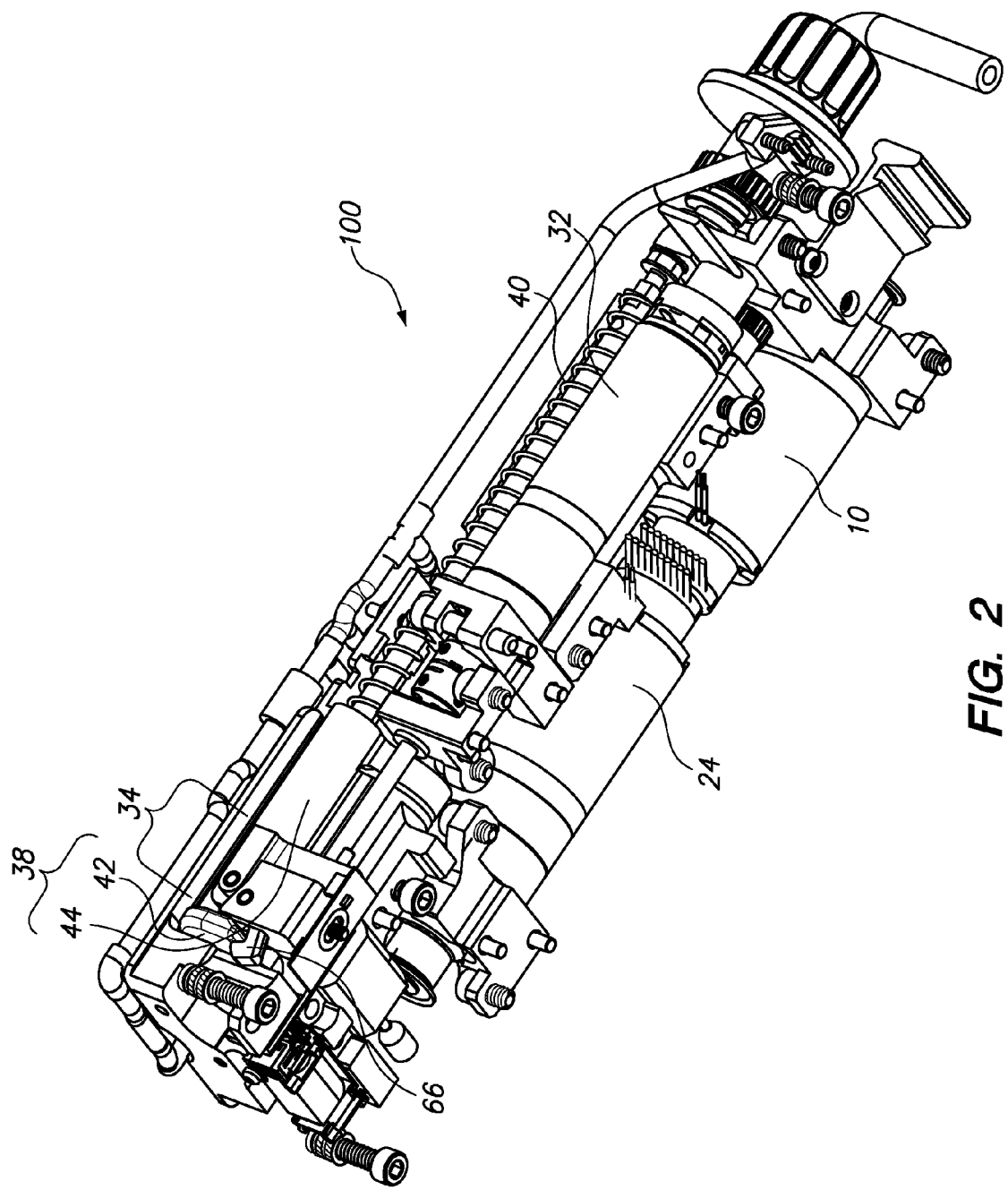
Figure 3:
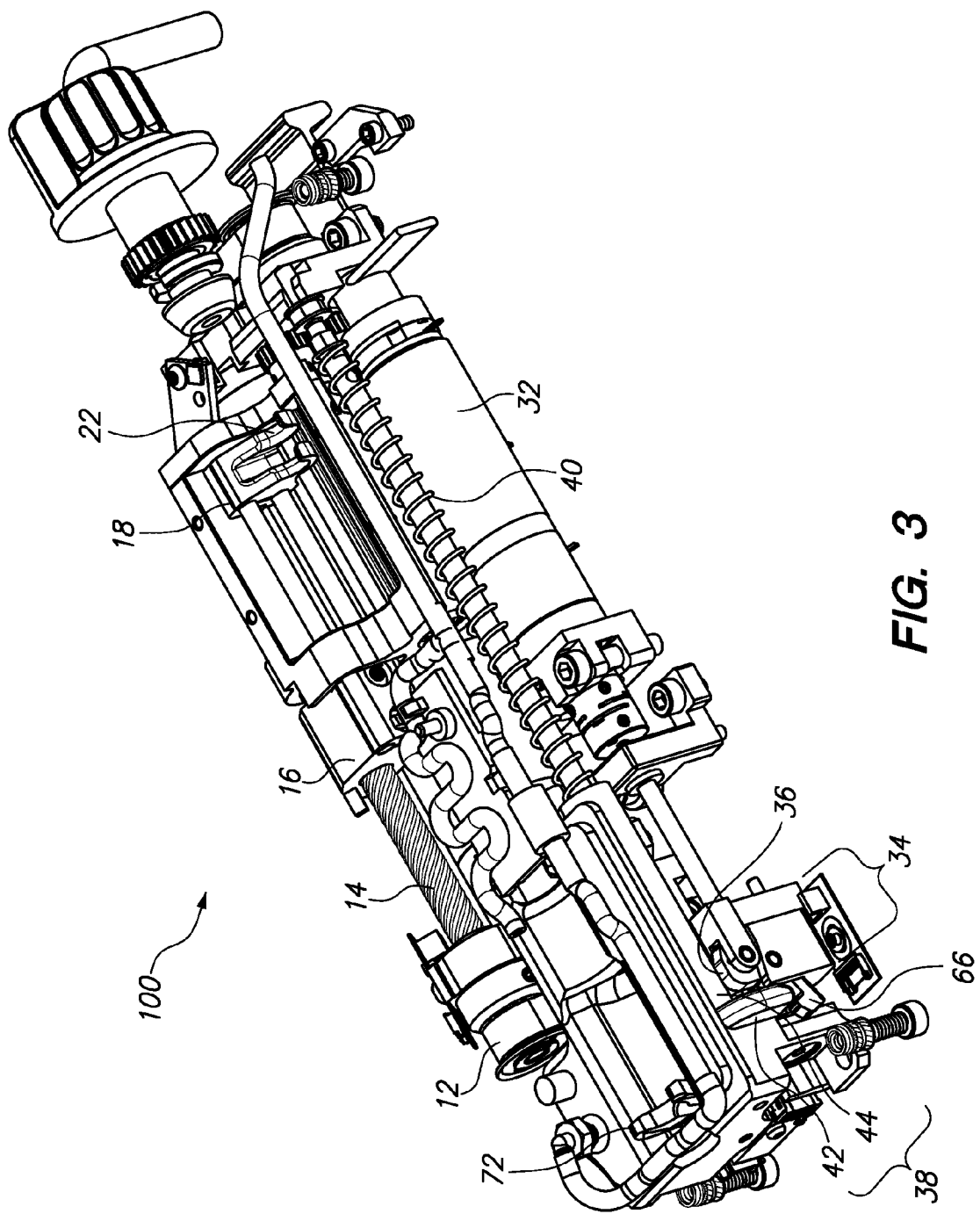
Figure 4:
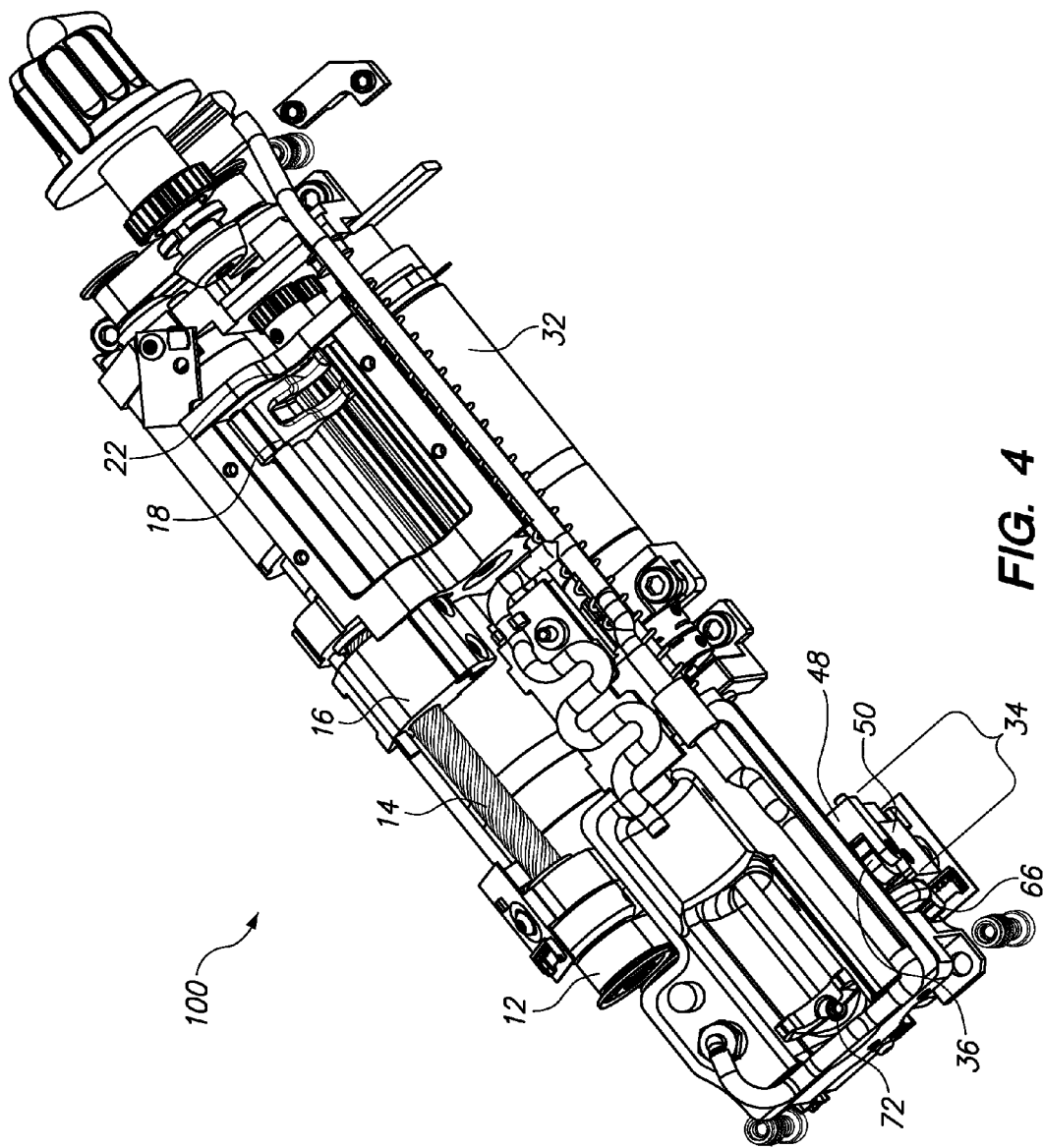
Figures 5, 6:
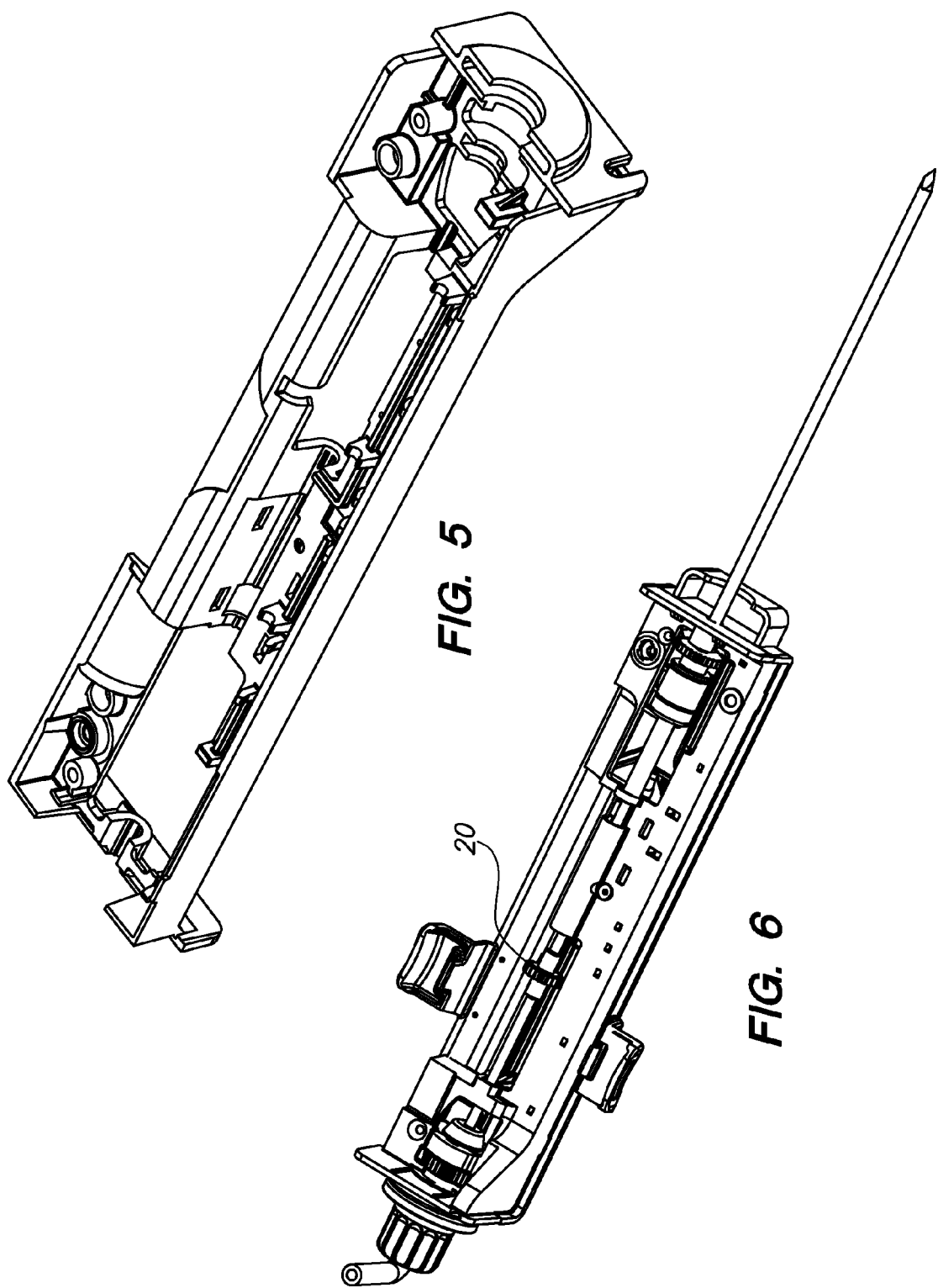
FIG. 5 is a perspective view of a portion of the bottom body of a two-part biopsy device according to one embodiment, with other components omitted for clarity.
FIG. 6 is a bottom perspective view of a top portion of a two-part biopsy device according to one embodiment, with select components omitted for clarity.

A portion of the bottom part 100 for holding the various carriages, gears, and motors is depicted in FIG. 5. FIG. 6 depicts a top part of the biopsy device including a needle set disposed in the top part. When the top and bottom 100 parts of the biopsy device are fitted together, the needle set (including the inner cannula the outer cannula) in the top part are operatively coupled to the various carriages, gears, and motors in the bottom part 100 (described below).

Figure 7:
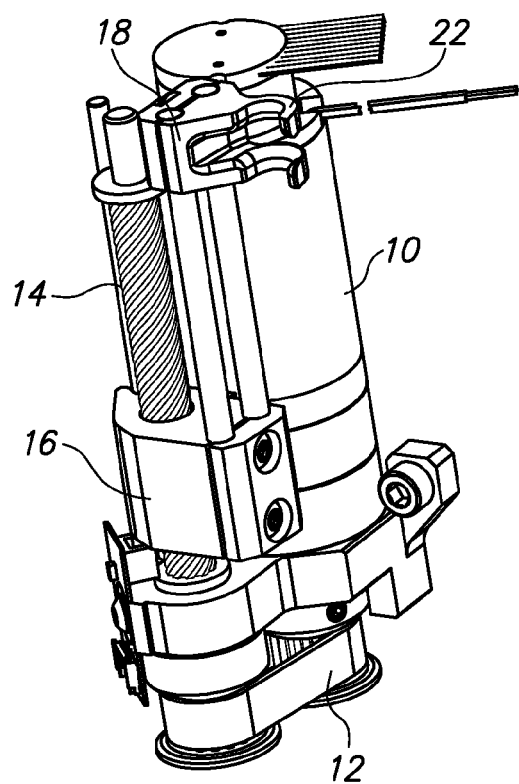
FIG. 7 is a perspective view of the inner cannula translation system according to one embodiment, with other components omitted for clarity.
Figure 8:
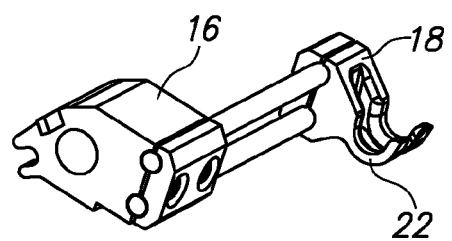
FIG. 8 is a perspective view of a nut, arm and cradle of the inner cannula translation system depicted in FIG. 7.

The bottom part 100 of the biopsy device includes three systems: an inner cannula translation system 102; an inner cannula rotation system 104; and an outer cannula arming/firing system 106. FIGS. 7 and 8 depict various components of the inner cannula translation system 102. FIG. 7 depicts the inner cannula translation motor 10 operatively coupled via a belt 12 to an inner cannula translation lead screw 14. The inner cannula translation lead screw 14 is in turn operatively coupled to an inner cannula translation nut 16 and arm 18, which are depicted in FIGS. 7 and 8. The inner cannula translation lead screw 14 is threaded through an opening in the inner cannula translation nut 16. The inner cannula translation nut 16 has threads on an inner surface surrounding the opening, and those threads are configured to interleave with complementary threads on an outer surface of the lead screw 14. Accordingly, rotation of the inner cannula translation lead screw 14 results in axial translation of the inner cannula nut 16 and the arm 18 attached thereto.

When the top and bottom 100 parts of the biopsy device are fitted together, a gear 20 (FIG. 9) coupled to a proximal portion of the inner cannula is operatively connected to a cradle 22 on the translation arm 18 (FIGS. 7 and 8), so that when the translation arm 18 moves axially (via its connection to the inner cannula translation nut 16) so does the inner cannula.

Upon receiving a signal from a controller (not shown), the inner cannula translation motor 10 rotates a belt 12 (FIG. 7), which rotates the inner cannula translation lead screw 14 (via belt 12), thereby axially translating the inner cannula translation nut 16 and arm 18, as described above. When the top and bottom 100 parts of the biopsy device are fitted together, axial translation of the inner cannula translation nut 16 and arm 18 moves the inner cannula in a corresponding axial direction. When the translation nut 16 and arm 18 reach an end of travel, the inner cannula translation motor 10 reverses direction, thereby reciprocating the inner cannula in an opposite axial direction.

Figure 9:
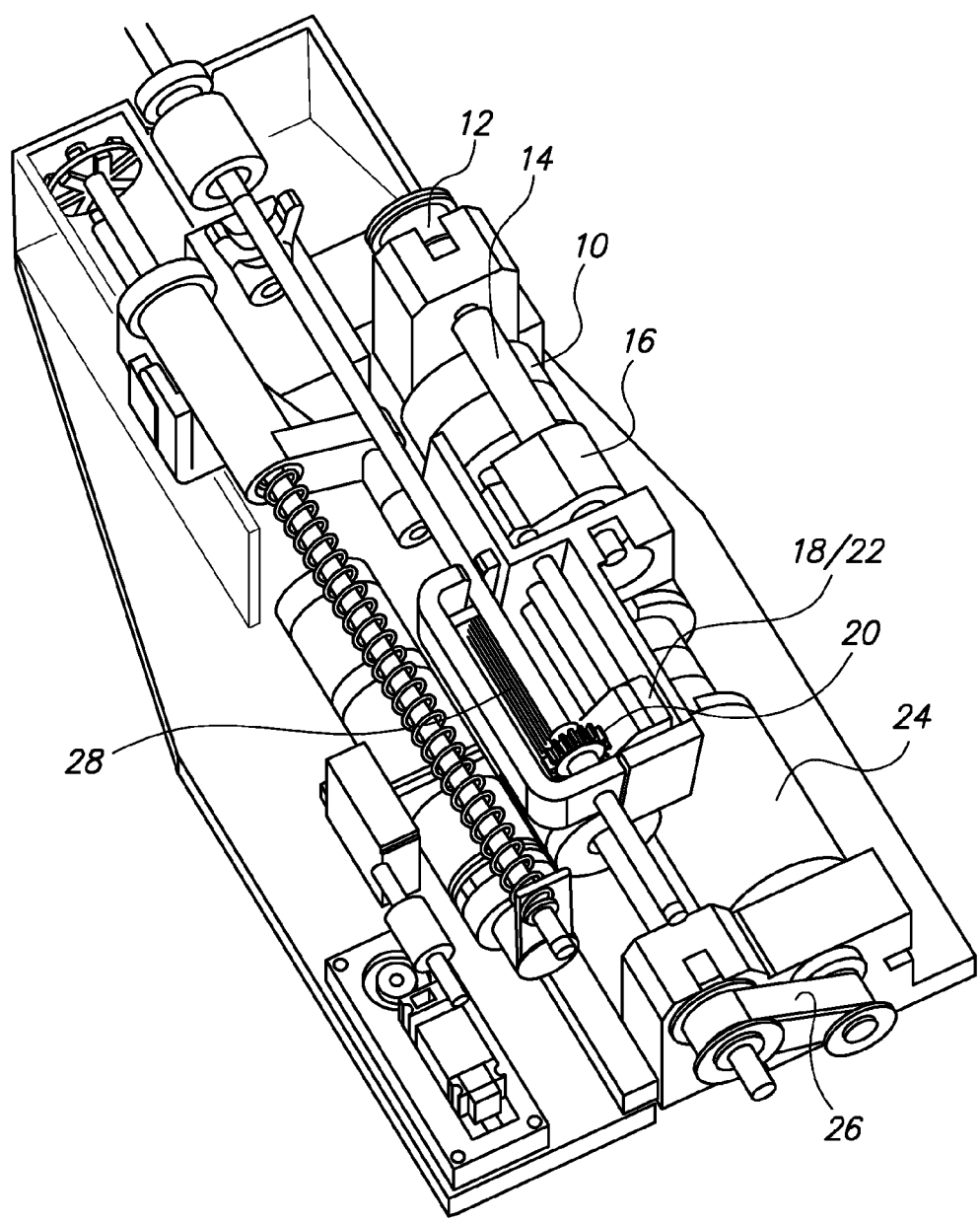
FIG. 9 is a perspective view of the bottom portion of a two-part biopsy device according to another embodiment, with select components omitted for clarity.

Various portions of the inner cannula rotation system 104 are depicted in FIGS. 9 and 10. FIG. 9 depicts the inner cannula rotation motor 24, which is operatively coupled to a belt 26, which is in turn operatively coupled to a pinion 28 (FIG. 10) via a shaft. When the top and bottom 100 parts of the biopsy device are fitted together, the pinion 28 is operatively coupled to the gear 20 (FIGS. 6 and 9) coupled to the proximal portion of the inner cannula. In particular, the gear 20 is axially (but not rotationally) constrained in the cradle 22 on the translation arm 18 of the inner cannula translation system 102. The top part of the biopsy device also includes a leaf spring (not shown), which urges the gear 20 in a downward direction toward the pinion 28, thereby ensuring that the gear 20 and the pinion 28 are operatively meshed together. Operatively meshing the gear 20 and pinion 28 together ensures that rotation of the pinion 28 results in rotation of the gear 20 and the inner cannula attached thereto in the opposite direction.

Upon receiving a signal from the controller (not shown), the inner cannula rotation motor 24 rotates the belt 26, which rotates the pinion 28, thereby rotating the gear 20 and the inner cannula attached thereto. The inner cannula also translates by way of the inner cannula translation motor 10, the belt 12, the inner cannula translation lead screw 14, and the inner cannula translation nut 16 and arm 18 as described above. The length of the pinion 28 is greater than the travel of the translation arm 18, thereby ensuring rotation of the gear 20 in the inner cannula throughout the axial travel of the inner cannula. Rotation of the inner cannula facilitates excision of tissue prolapsing through the tissue receiving aperture by the annular blade at the open distal end of the inner cannula.

The outer cannula arming/firing system 106 is illustrated in FIGS. 11-26B. The outer cannula arming/firing system 106 includes an arming motor 32 (FIGS. 11-14), operatively connected to an latching assembly 34, a sled 38, and a firing spring 40 (FIGS. 12 and 15-23). When the top (disposable) and bottom (reusable) 100 parts of the biopsy device are fitted together, the sled 38 is operatively connected to the outer cannula via a fork (shown in FIGS. 1, 3, 4, 11 and 14) such that axial movement of the sled 38 results in corresponding axial movement of the outer cannula. This operative coupling allows the outer cannula arming/firing system 106 to axially arm and fire the outer cannula by moving the sled 38, as described below.

Figure 12:
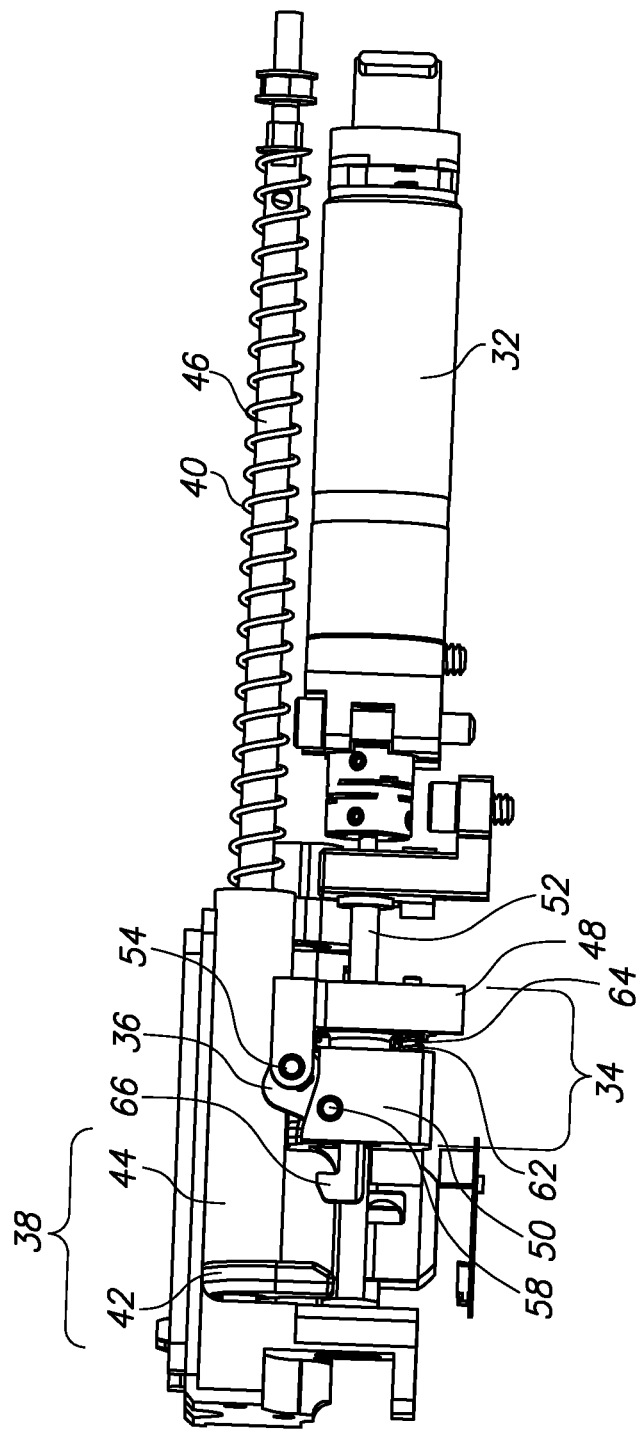
FIG. 12 is a side view of the outer cannula arming/firing mechanism depicted in FIG. 11, with select components omitted for clarity.
Figure 13:
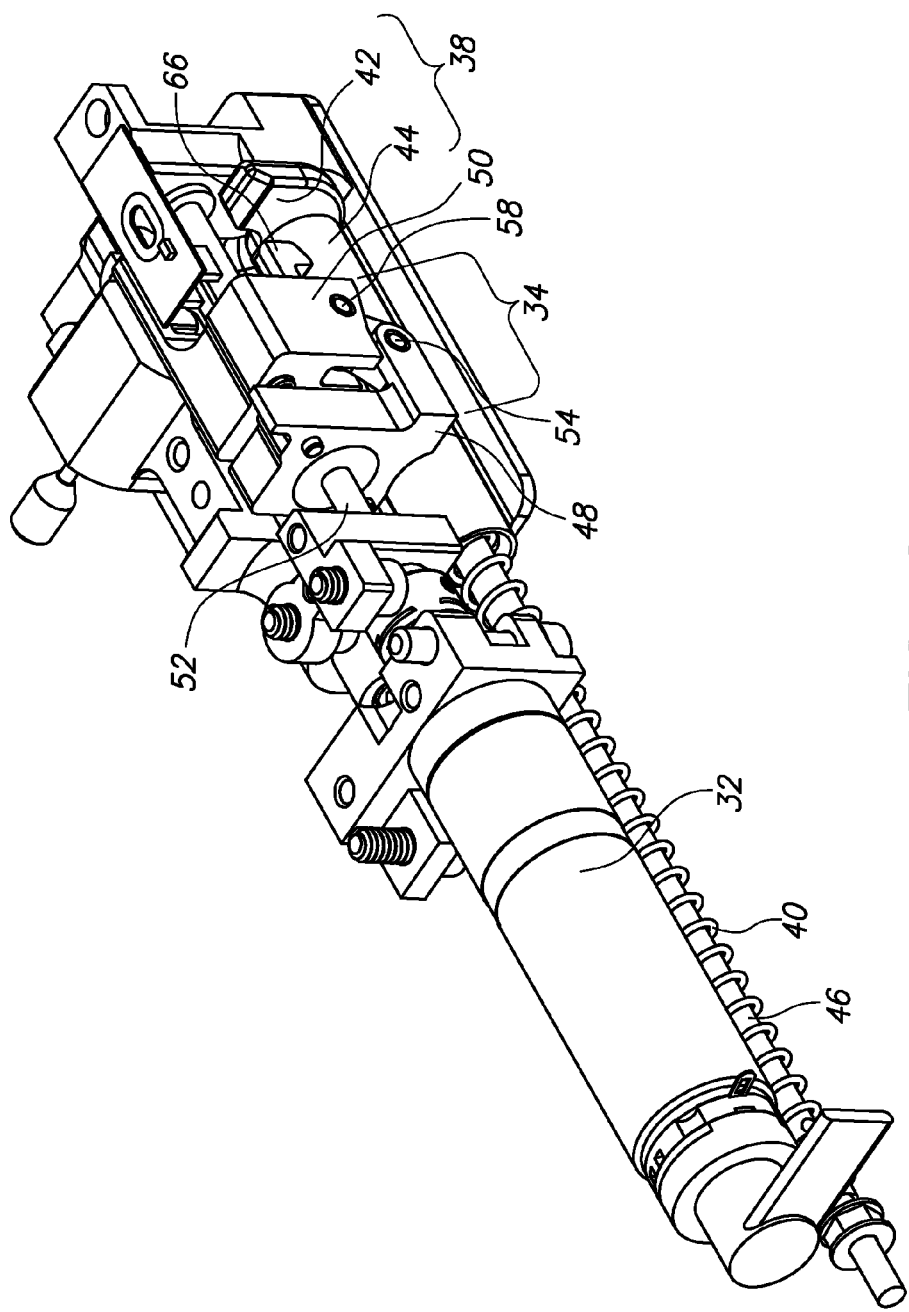
Figure 14:
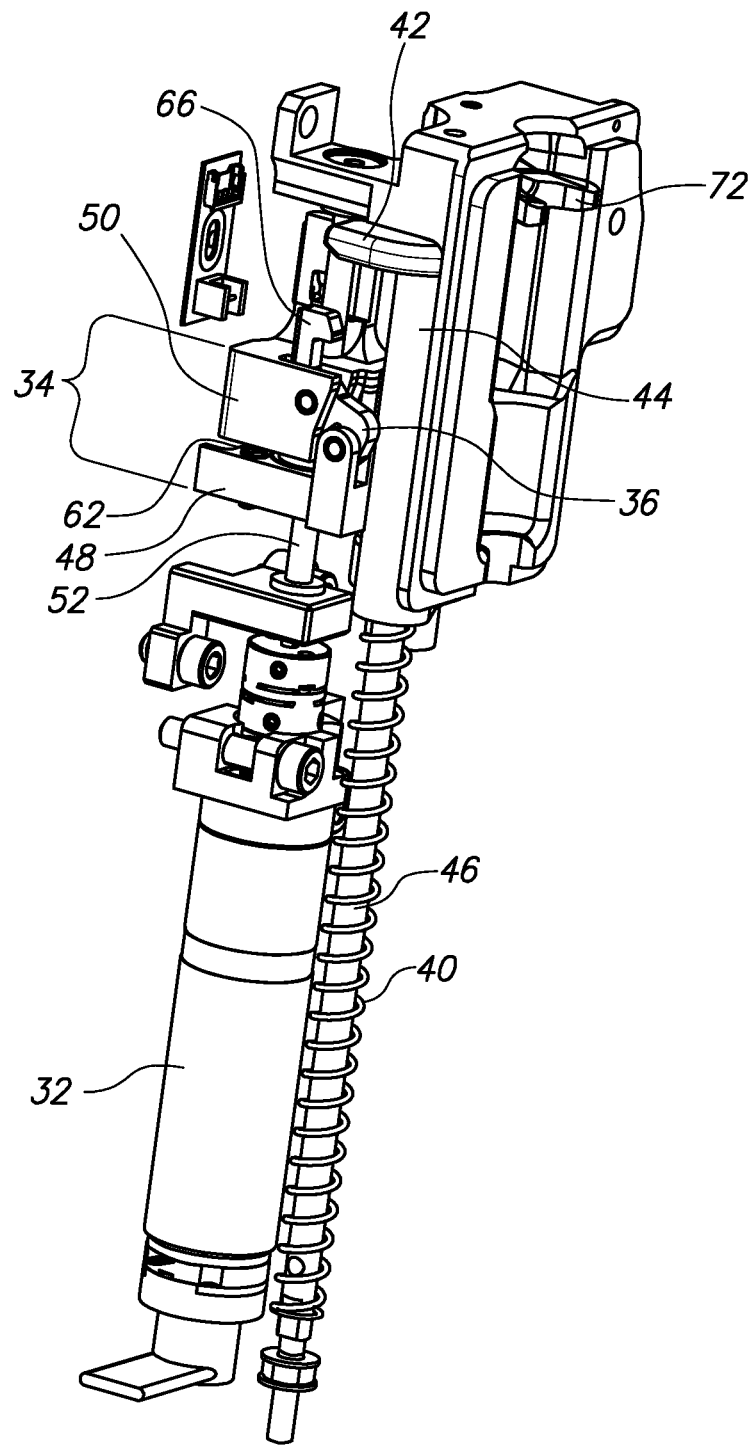
Figure 15:
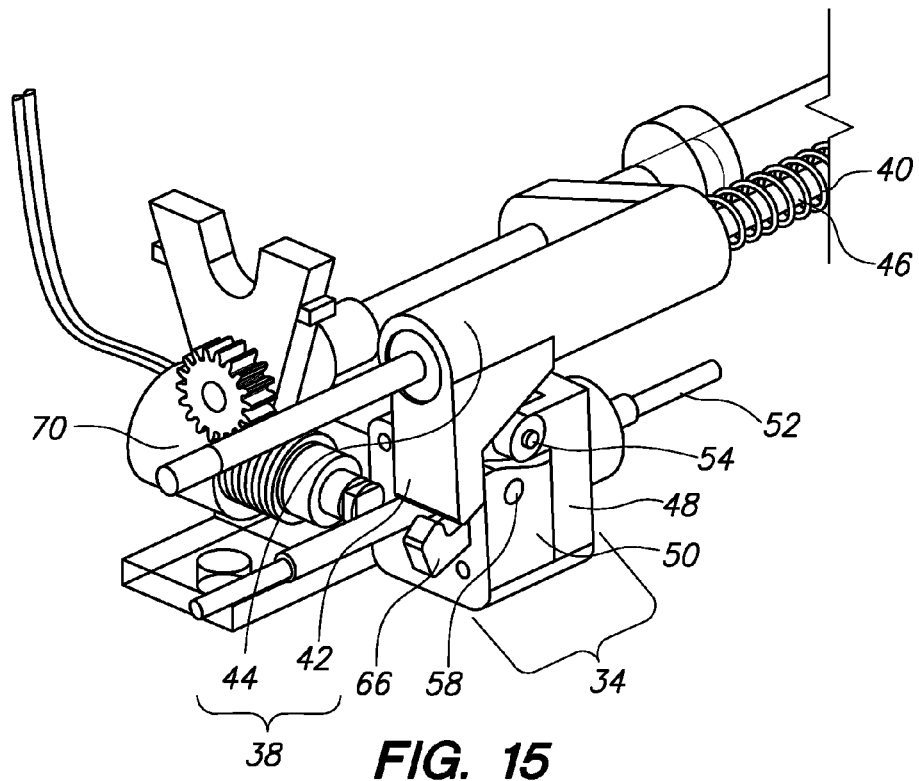
FIGS. 15 and 16 are perspective views of an outer cannula arming/firing mechanism according to one embodiment, with other components omitted for clarity.
Figure 16:
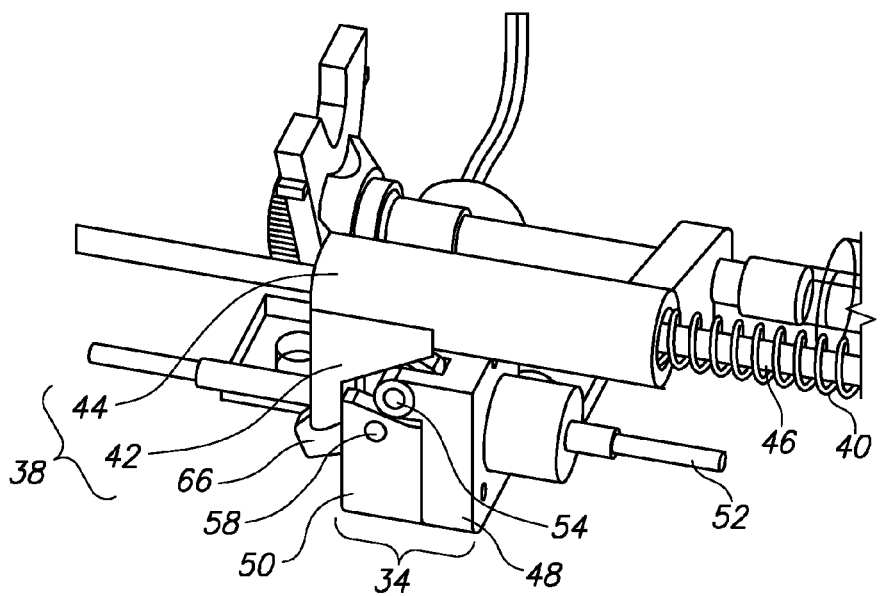
Figure 17:
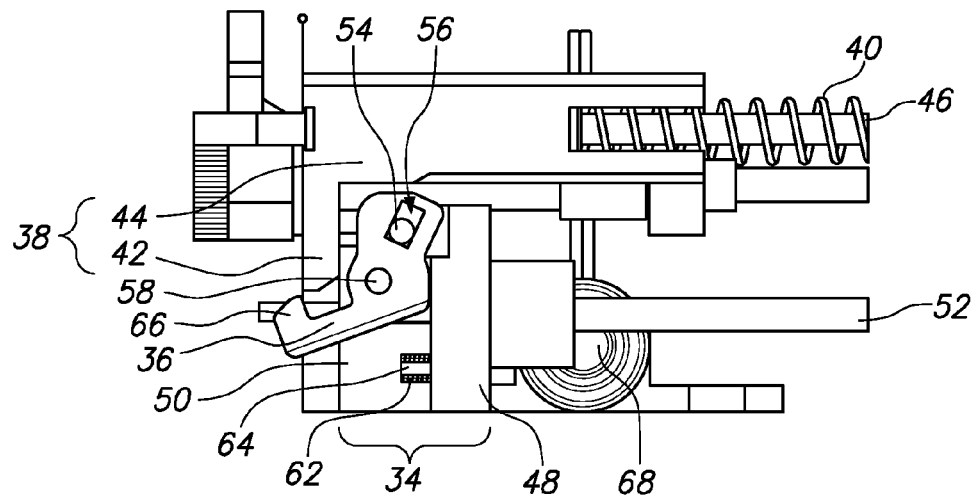
FIGS. 17-23 are side views of the outer cannula arming/firing mechanism depicted in FIG. 15 in sequential steps of an arming/firing cycle, with other components omitted for clarity.

The latching assembly 34 includes an outer cannula translation nut (or "outer cannula translation member") 48, a distal pin member (or "latch base") 50 and a latch (or "latch arm") 36 operatively coupled to each other, as shown in FIGS. 12 and 17, and described below. The latch 36 is configured to interact with an orthogonally extending member (or "laterally extending catch arm") 42 of the sled 38. The sled 38 (or "instrument drive member") comprises the orthogonally extending member 42 and a tubular member 44 disposed around a sled shaft 46. A firing spring 40 is disposed around the sled shaft 46 and operatively coupled to the tubular member 44, such that axial movement of the sled 38 in a proximal direction compresses the firing spring 40. The latch 36 is pivotally mounted in the latching assembly 34 so that it can pivot in the latching assembly. The latch 36 is biased to engage the orthogonally extending member 42 of the sled 38, as described below.

As shown in FIG. 12, the outer cannula translation nut 48 and the distal pin member 50 are movably (in an axial direction) connected to each other by the latch 36, as described below. The outer cannula translation nut 48 and the distal pin member 50 are slidably disposed on a nut shaft 52, with the distal pin member 50 distal of the outer cannula translation nut 48 (relative to the biopsy device).

In particular, the outer cannula translation nut 48 has an inverted "L" shaped profile, as shown in side view in FIG. 12 and in series of longitudinal cross-sectional views in FIGS. 17-23. The "L" shaped outer cannula translation nut 48 is inverted in the biopsy device such that the shorter leg of the "L" is disposed closer to the top part of the biopsy device, and the longer leg of the "L" is disposed closer to the proximal end of the biopsy device. When viewed from above as in FIG. 4, it is apparent that the short leg of the "L" shaped outer cannula translation nut 48 also forms a fork in which a part of the latch 36 is disposed.

Figure 24:
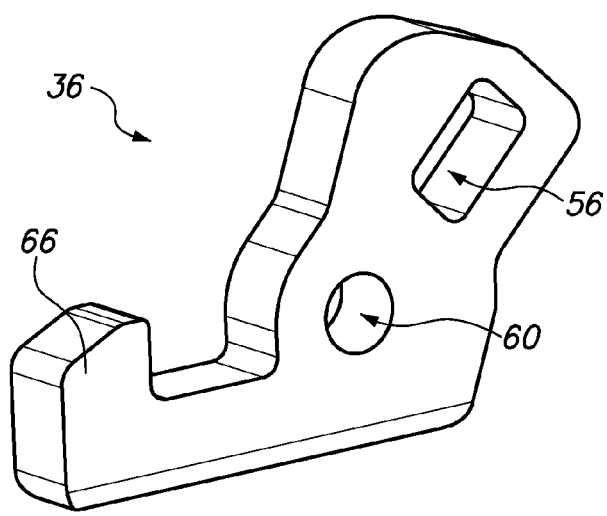
FIG. 24 is a perspective view of a latch of an outer cannula arming/firing mechanism according to one embodiment.
Figure 25:
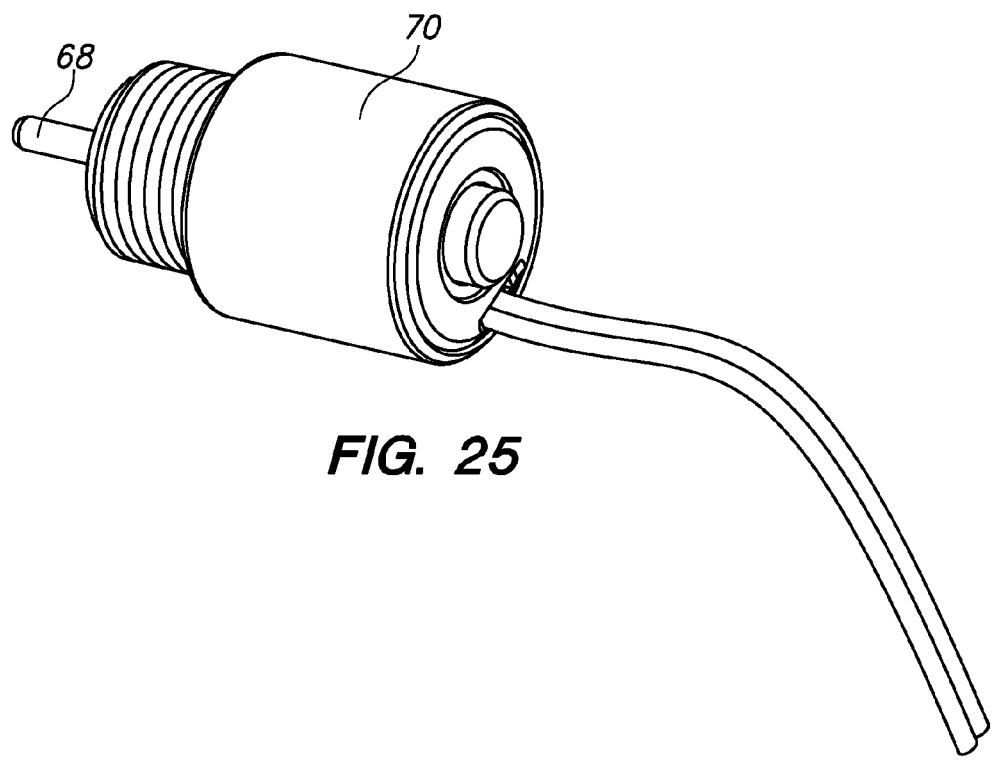
FIG. 25 is a perspective view of a detent and a solenoid of an outer cannula arming/firing mechanism according to one embodiment.

As shown in cross-section in FIG. 17, a proximal peg 54 movably connects the latch 36 to the outer cannula translation nut 48 of the latching assembly 34. The proximal peg 54 passes through a pin-shaped opening in the outer cannula translation nut 48 and a slot 56 in a proximal portion of the latch 36, as shown in FIGS. 12 and 17. The slot 56 is generally rectangular with a width approximately equal to the cross-sectional diameter of the proximal peg 54, and a length approximately 1.5 times the cross-sectional diameter of the proximal peg 54, as shown in FIGS. 17 and 24. When the latch 36 is fitted into the latching assembly 34 and the slot 56 is viewed from the side, the proximal end of the slot 56 also extends upward and the distal end of the slot 56 also extends downward, as shown in FIG. 17. The size and shape of the slot 56 in the latch 36 allows the proximal peg 54 to pivot and translate in the slot 56.

The distal pin member 50 has an approximately rectangular profile as shown in FIGS. 12 and 17. A part of the latch 36 (different than the part disposed in the outer cannula translation nut 48 of the latching assembly 34) is disposed in the distal pin member 50 of the latching assembly 34, as shown in FIGS. 17. A distal pin 58 rotatably connects the latch 36 to the distal pin member 50 of the latching assembly 34. The distal pin 58 passes through a pin-shaped opening in the distal pin member 50 and an opening 60 in the latch 36, as shown in FIGS. 17 and 24. The opening 60 is approximately the same size and shape as the cross-section of the distal pin 58. The size and shape of the opening 60 in the latch 36 allows the distal pin 58 to rotate, but not translate, in the opening 60.

Figure 18:
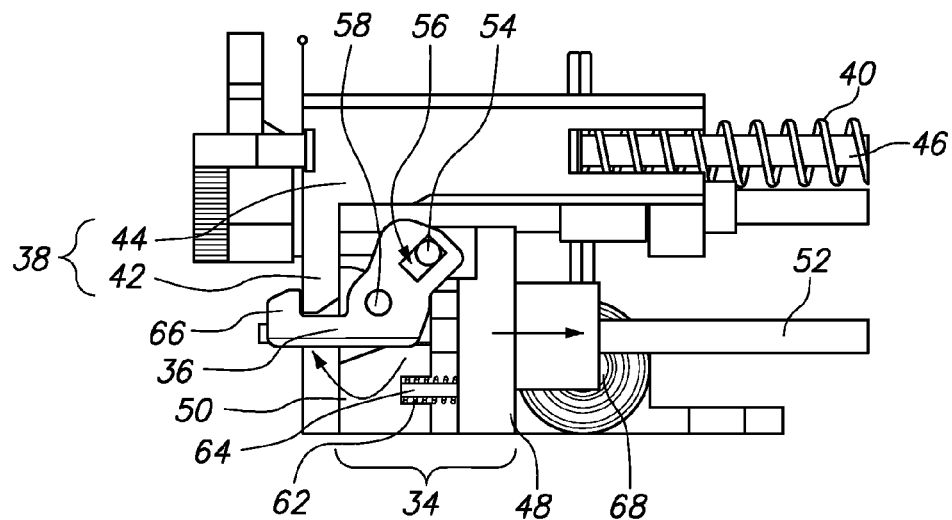
Figure 20:
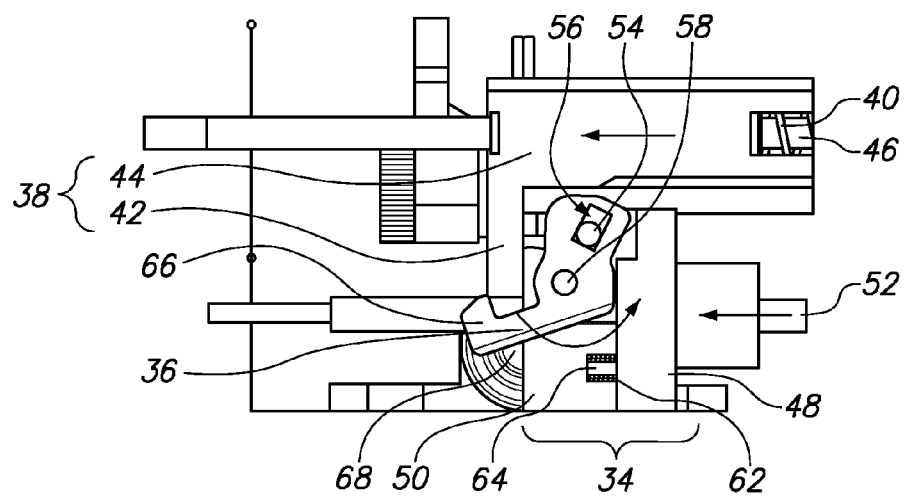
Figure 22:
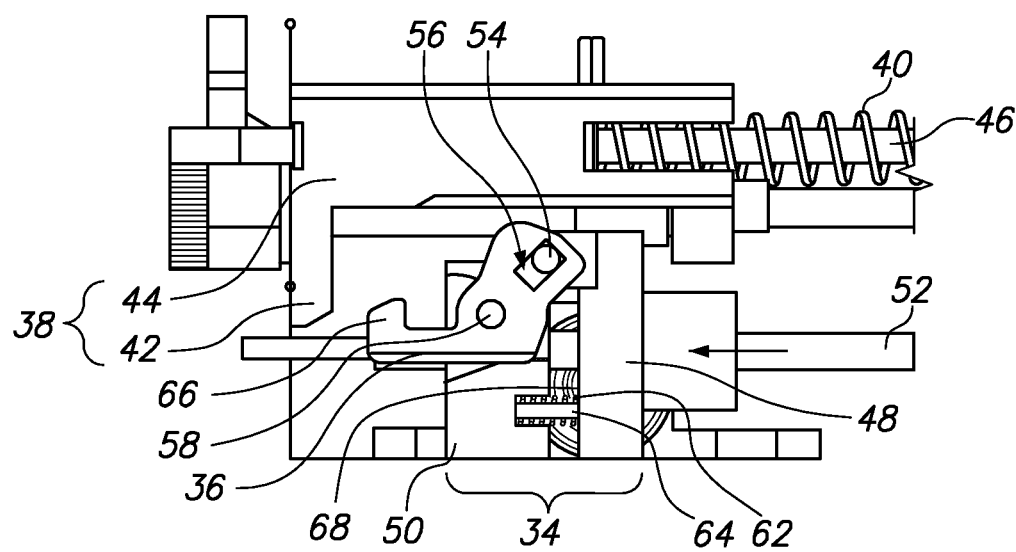

As shown in FIGS. 12 and 17, the outer cannula translation nut 48 and the distal pin member 50 are also operatively coupled to each other by a nut spring (or "biasing spring") 62 on a dowel 64. The nut spring 62 and the dowel 64 are disposed in respective recesses in the outer cannula translation nut 48 and the distal pin member 50 of the latching assembly 34. The proximal peg 54 and distal pin 58 in the slot 56 and opening 60, together with the nut shaft 52 on which the outer cannula translation nut 48 and the distal pin member 50 are mounted, prevent the outer cannula translation nut 48 and the distal pin member 50 from separating from each other sufficiently to allow the dowel 64 and the nut spring 62 to exit the recesses. The nut spring 62 is biased in an expanded configuration, as shown in FIGS. 18, 20 and 22.

With the nut spring 62 in its expanded configuration, the outer cannula translation nut 48 and the distal pin member 50 are pushed apart from each other. This in turn pushes the proximal peg 54 in the proximal direction. Because the proximal end of the slot 56 also extends upward, pushing the proximal peg 54 in the proximal direction in the slot 56 also pushes the proximal peg 54 upward in the slot 56. The proximal peg 54 and distal pin 58 are fixed in the up/down direction by being connected to the outer cannula translation nut 48 and the distal pin member 50 of the latching assembly 34, which are themselves fixed by the nut shaft 52. As a result, when the proximal peg 54 is pushed in the proximal direction by the expanding nut spring 62, the latch 36 pivots clockwise about the distal pin 58 in the opening 60 so that the proximal portion of the latch 36, which includes the slot 56, moves downward. A distal portion of the latch 36 generally opposite of the slot 56 includes a catch 66, which is configured to interfere with the orthogonally extending member 42 of the sled 38 when the latch 36 is pivoted into a closed position. When the latch 36 is pivoted such that the slot 56 moves downward, the catch 66 on the opposite side of the latch 36 moves upward into the closed position in which it can interfere with the orthogonally extending member 42.

When the outer cannula translation nut 48 and the distal pin member 50 are pushed together (as shown in FIGS. 17, 20, 21 and 23) by nut shaft 52 they compress the nut spring 62. Further, pushing the outer cannula translation nut 48 and the distal pin member 50 together pushes the proximal peg 54 in the distal direction. Because the distal end of the slot 56 also extends downward, pushing the proximal peg 54 in the distal direction in the slot 56 also pushes the proximal peg 54 downward in the slot 56. This in turn causes the latch 36 to pivot counterclockwise about the distal pin 58 in the opening 60 so that the proximal portion of the latch 36, which includes the slot 56, moves upward, thereby causing the catch 66 on the opposite side of the latch 36 to move downward into an open position in which it can no longer interfere with the orthogonally extending member 42.

The arming motor 32 is operatively connected to the outer cannula translation nut 48 via a nut shaft 52 (FIG. 12). The nut shaft 52 has threads on an external surface thereof. The nut shaft 52 is threaded through an opening in the outer cannula translation nut 48. The outer cannula translation nut 48 has threads on an inner surface surrounding the opening, and those threads are configured to interleave with complementary threads on an outer surface of the nut shaft 52. In this manner, rotation of the arming motor 32 causes axial translation of the outer cannula translation nut 48 via the threaded nut shaft 52. In the embodiment depicted in FIGS. 15-23, the proximal portion of the outer cannula translation nut 48 includes a proximally extending cylinder, which also defines an opening and includes internal threads configured to interleave with complementary threads on an outer surface of the nut shaft 52. The nut shaft 52 also passes through an unthreaded opening in the distal pin member 50, thereby limiting the motion of the distal pin member 50 to along the longitudinal axis.

The disclosed biopsy device uses the above-described features of the latching assembly 34, latch 36 and sled 38 to both arm and fire the sled 38, and the outer cannula operatively coupled thereto, using only the arming motor 32. FIG. 17 depicts a state in the outer cannula firing process in which the sled 38 and the outer cannula (not shown) are in their distal most (i.e., fired) position and the firing spring 40 is in its most expanded position. The outer cannula translation nut 48 and the distal pin member 50 are driven together by the arming motor 32, thereby pivoting the latch 36 counterclockwise such that it does not engage the orthogonally extending member 42 of the sled 38. With the distal pin member 50 prevented from moving distally by the orthogonally extending member 42 of the sled 38, when the arming motor 32 drives the outer cannula translation nut 48 distally toward the distal pin member 50, the proximal peg 54 pivots the latch 36 about the distal pin 58 such that the catch 66 on the latch 36 pivots away from the orthogonally extending member 42 and into the open position. Pivoting of the catch 66 away from the orthogonally extending member 42 disengages the latch 36 from the orthogonally extending member 42 and releases the sled 38. Driving the outer cannula translation nut 48 into the distal pin member 50 also compresses the nut spring 62.

Upon receiving an arming signal from the controller (e.g., a processor), the arming motor 32 pulls the outer cannula translation nut 48 in a proximal direction, thereby moving the outer cannula translation nut 48 proximally away from the distal pin member 50, as shown in FIG. 18. Movement of the outer cannula translation nut 48 and the distal pin member 50 apart from each other is also facilitated by expansion of the compressed nut spring 62, which is biased to separate the two portions 48, 50. When the outer cannula translation nut 48 and the distal pin member 50 are pulled and pushed apart, the proximal peg 54 pivots the latch 36 about the distal pin 58 such that the catch 66 on the latch 36 pivots toward the orthogonally extending member 42 and into the closed position. Consequently, the latch 36 springs into engagement with the orthogonally extending member 42 of the sled 38.

Figure 19:
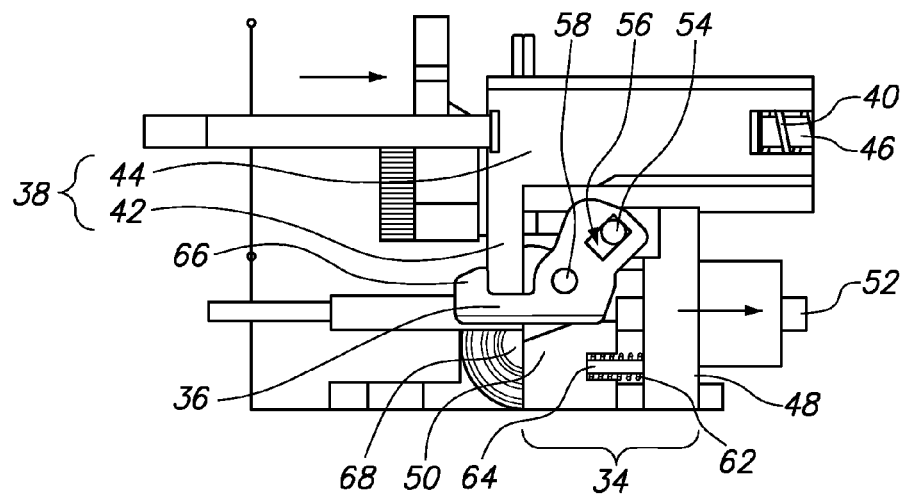

The arming motor 32 continues to drive the outer cannula translation nut 48 in a proximal direction, which pulls the distal pin member 50 in the proximal direction via the proximal peg 54 and distal pin 58 and the latch 36, as shown in FIG. 19. Further proximal movement pulls the sled 38 in a proximal direction via the catch 66 and the orthogonally extending member 42, thereby pulling the outer cannula in the proximal direction, and compressing the firing spring 40. In this manner, the outer cannula arming/firing system 106 arms the biopsy device for firing. The proximal, armed position of the system 106 is depicted in FIG. 19.

Figure 21:
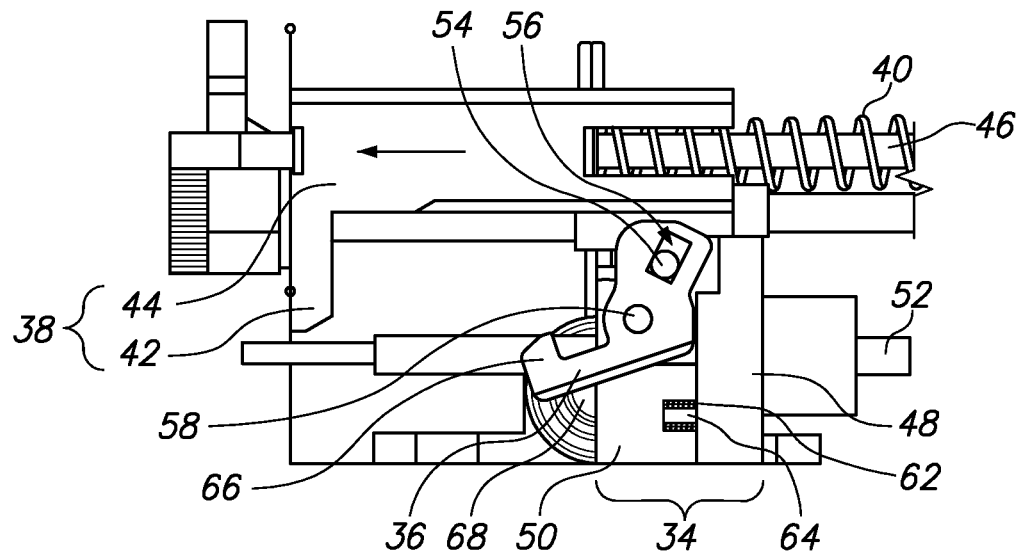
Figure 26A:
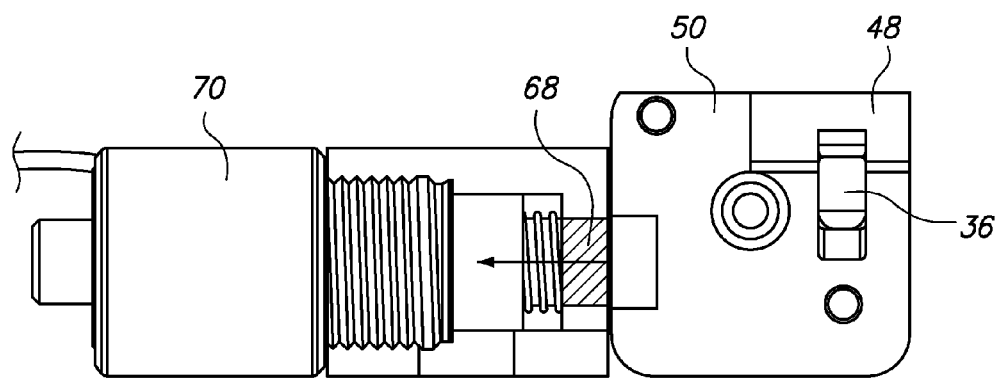
FIGS. 26A and 26B are two distal end views of the outer cannula arming/firing mechanism depicted in FIG. 15 with the outer cannula nut in slidably (FIG. 26A) and fixedly (FIG. 26B) coupled states, respectively.
Figure 26B:
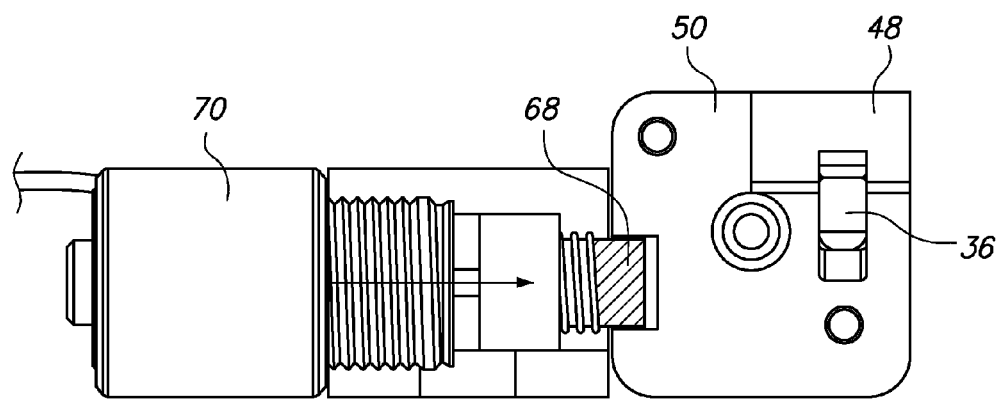

When a user fires the biopsy device, a solenoid 70 (FIG. 25) first extends a detent 68 to prevent distal movement of the latching assembly 34, as shown in FIGS. 26A and 26B. In FIG. 26A, the solenoid 70 has refracted the detent 68 out of the path of travel of the latching assembly 34. In FIG. 26B, the solenoid 70 has extended the detent 68 into the path of travel of the latching assembly 34, thereby preventing distal movement of the latching assembly 34. Then the arming motor 32 drives the outer cannula translation nut 48 in a distal direction, thereby squeezing the outer cannula translation nut 48 and the distal pin member 50 together (against the extended detent 68), as shown in FIGS. 20 and 21. This compresses the nut spring 62 and pivots the latch 36 away from engagement with the orthogonally extending member 42, as described above with respect to FIG. 17, thereby releasing the sled 38 and the firing spring 40. In the state depicted in FIG. 20, the sled 38, including the orthogonally extending member 42 and the tubular member 44, are slidably coupled to the sled shaft 46. The latching assembly 34, including the outer cannula translation nut 48 and the distal pin member 50, and the latch 36, are fixedly coupled to the nut shaft 52 because they are driven by the arming motor 32 into the detent 68.

The potential energy stored in the compressed firing spring 40 (which exerts a force of about 10 pounds on the sled 38) drives the slidably coupled sled 38, including the tubular member 44 and the orthogonally extending member 42, in a distal direction along the sled shaft 46, thereby firing the outer cannula distally, as depicted in FIG. 21. The fixedly coupled latching assembly 34 and latch 36 remain fixed on the nut shaft 52 against the detent 68. After the sled 38 is fired, the arming motor 32 pulls the outer cannula translation nut 48 proximally until the pressure of the distal pin member 50 against detent 68 is sufficiently released to allow the solenoid 70 to retract the detent 68 out of engagement with the latching assembly 34. This can be either before or after the nut spring 62 is fully expanded. After the detent 68 is retracted, the latching assembly 34 and latch 36 are slidably coupled (in the distal direction) to the nut shaft 52.

As shown in FIG. 22, the arming motor 32 then reverses direction and pushes the slidably coupled latching assembly 34 and latch 36 in a distal direction along the nut shaft 52. While the arming motor 32 pushes the latching assembly 34 and latch 36 along the nut shaft 52, the nut spring 62 forces the outer cannula translation nut 48 and the distal pin member 50 apart from each other and pivots the catch 66 of the latch 36 upward into the closed position.

Figure 23:
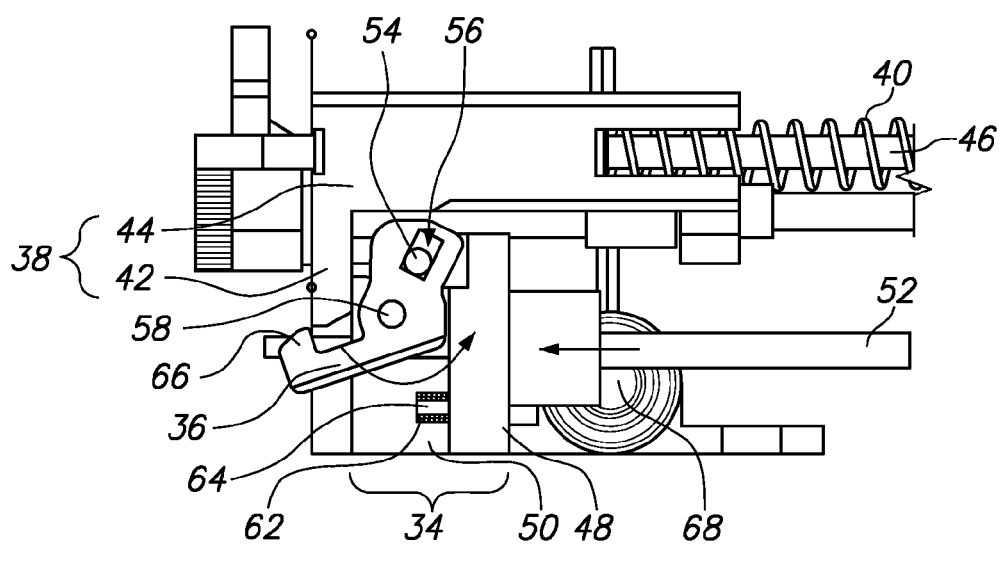

As shown in FIG. 23, further distal movement of the outer cannula translation nut 48 and latch 36 moves the distal pin member 50 into contact with the orthogonally extending member 42 of the sled 38, thereby preventing further distally movement of the distal pin member 50 of the latching assembly 34. Continued distal movement of the outer cannula translation nut 48 pivots the catch of the latch 36 downward and brings the outer cannula translation nut 48 and the distal pin member 50 together thereby compressing the nut spring 62. After the outer cannula translation nut 48 and the distal pin member 50 are brought into contact with each other, the latching assembly 34 and latch 36 are fixed coupled to the nut shaft 52 by the arming motor 32 and the orthogonally extending member 42 of the sled 38. This returns the outer cannula arming/firing system 106 to the fired position depicted in FIG. 17.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A biopsy instrument driver, comprising:
   an instrument drive member coupled to a support structure and having a laterally extending catch arm, the drive member being movable relative to the support structure between a distal, fired position and a proximal, armed position;
   a motor coupled to the support structure and having a rotatable output;
   a drive shaft rotatably coupled to the support structure, the drive shaft comprising or otherwise being operatively connected to the motor output such that activation of the motor rotates the drive shaft;
   a translating member threadably coupled to the drive shaft, such that rotation of the drive shaft causes axial translation of the translating member along the drive shaft relative to the support structure;
   a latch base movably coupled to the support structure and operatively associated with the translating member; and
   a latch arm movably coupled to the latch base, the latch arm having a distal portion configured to selectively engage and retain the instrument drive member catch arm, and a proximal portion operatively coupled to the translating member, such that movement of the translating member along the drive shaft relative to the latch base moves latch arm distal portion.

2. The biopsy instrument driver of claim 1, wherein the latch arm is coupled to the latch base by a pin, such that the latch arm may pivot about the pin relative to the latch base.

3. The biopsy instrument driver of claim 2, wherein the proximal portion of the latch arm comprises a slot through which a peg extending from the translating member extends, such that movement of the translating member relative to the latch base causes a corresponding movement of the peg within the slot to thereby pivot the latch arm relative to the latch base between an open position and a closed position.

4. The biopsy instrument driver of claim 3, the latch base being movable relative to the support structure between a most-distal position and a most-proximal position, wherein when the latch base is in the most-distal position and the drive member is in the fired position, the latch arm may be moved from the open position to the closed position to thereby retain the drive member catch arm, and wherein when the latch base is moved to the most-proximal position with the latch arm retaining the drive member catch arm, the drive member is thereby moved to its armed position.

5. The biopsy instrument driver of claim 4, further comprising a firing spring operatively coupled to the drive member, wherein the firing spring is loaded as the drive member is moved from the fired position to the armed position.

6. The biopsy instrument driver of claim 5, further comprising a biasing spring interposed between the latch base and the translating member, the biasing spring applying a spring force to separate the latch base from the translating member.

7. The biopsy instrument driver of claim 6, the motor being a reversible output direction motor, such that activation of the motor in a first motor output direction moves the translating member along the drive shaft in a distal direction relative to the support structure, and activation of the motor in a second motor output direction opposite the first motor output direction moves the translating member along the drive shaft in a proximal direction relative to the support structure, the instrument driver further comprising a controller configured to control activation and output direction of the motor.

8. The biopsy instrument driver of claim 7, further comprising a solenoid configured to selectively prevent distal movement of the latch base when the latch base is in the most-proximal position, wherein the controller controls activation of the solenoid.

9. The biopsy instrument driver of claim 8, wherein when the drive member is in the fired position, the controller is configured to arm the drive member by activating the motor in the first output direction to move the translating member in a distal direction relative to the support structure, thereby also moving the latch base in a distal direction via the biasing spring, until the latch base is in the most-distal position, wherein continued distal movement of the translating member compresses the biasing spring against latch base, with corresponding distal travel of the peg through the latch arm slot pivoting the latch arm into the open position; and activating the motor in the second output direction to move the translating member in a proximal direction relative to the support structure, the latch base remaining in the most-distal position until the bias spring restores to a non-compressed state, and cause corresponding proximal travel of the peg through the latch arm slot pivoting the latch arm into the closed position to thereby engage and retain the drive member catch arm, the peg thereafter pulling the respective latch arm, latch base, and drive member proximally in response to continued proximal movement of the translating member, until the latch base is in the most-proximal position and drive member in the armed position, with the firing spring in a loaded condition.

10. The biopsy instrument driver of claim 9, wherein when the driver member is retained in the armed position by the respective latch arm and latch base, the controller is configured to fire the drive member distally by activating the solenoid to thereby retain the latch base in the most-proximal position to thereby prevent distal movement of the latch base relative to the support structure; and activating the motor in the first output direction to move the translating member in a distal direction relative to the latch member, thereby compressing the biasing spring and moving the peg distally through the latch arm slot to pivot the latch arm from the closed position to the open position, thereby releasing the drive member catch arm.

11. The biopsy instrument driver of claim 1, the support structure comprising or otherwise being coupled to a drive unit housing.

* * * * *